United States Patent
Hu et al.

(10) Patent No.: US 11,209,362 B2
(45) Date of Patent: Dec. 28, 2021

(54) FLUORESCENT PROBE FOR DETECTING SULFENYLATED PROTEIN, PREPARATION METHOD THEREOF, AND APPLICATION THEREOF

(71) Applicant: CHONGQING MEDICAL UNIVERSITY, Chongqing (CN)

(72) Inventors: Xiaolei Hu, Chongqing (CN); Xiaolan Yang, Chongqing (CN); Yibing Yin, Chongqing (CN); Xiaomian Wu, Chongqing (CN); Fei Liao, Chongqing (CN); Jinpeng Lu, Chongqing (CN); Juqiong Li, Chongqing (CN)

(73) Assignee: CHONGQING MEDICAL UNIVERSITY, Chongqing (CN)

( * ) Notice: Subject to any disclaimer, the term of this patent is extended or adjusted under 35 U.S.C. 154(b) by 0 days.

(21) Appl. No.: 16/329,941

(22) PCT Filed: May 4, 2018

(86) PCT No.: PCT/CN2018/085697
§ 371 (c)(1),
(2) Date: Mar. 1, 2019

(87) PCT Pub. No.: WO2018/228079
PCT Pub. Date: Dec. 20, 2018

(65) Prior Publication Data
US 2020/0096444 A1    Mar. 26, 2020

(30) Foreign Application Priority Data

Jun. 13, 2017 (CN) .......................... 201710444443.3

(51) Int. Cl.
*G01N 21/00* (2006.01)
*G01N 21/64* (2006.01)
(Continued)

(52) U.S. Cl.
CPC ....... *G01N 21/6428* (2013.01); *C07C 303/32* (2013.01); *C09K 11/06* (2013.01);
(Continued)

(58) Field of Classification Search
CPC .................................................. G01N 21/6428
(Continued)

(56) References Cited

U.S. PATENT DOCUMENTS

| 4,120,892 A | 10/1978 | Poletto et al. | |
| 2009/0253646 A1 * | 10/2009 | Magnani ............ | A61K 31/7034 514/35 |

FOREIGN PATENT DOCUMENTS

| CN | 1103533 A | 6/1995 |
| CN | 103102338 A | 5/2013 |

(Continued)

OTHER PUBLICATIONS

Dhar et al. "Antitumour activity of suramin analogues in human tumour cell lines and primary cultures of tumour cells from patients" European Journal of Cancer 36 (2000) 803-809 (Year: 2000).*

(Continued)

*Primary Examiner* — Christine T Mui
*Assistant Examiner* — Emily R. Berkeley
(74) *Attorney, Agent, or Firm* — Rimon, P.C.

(57) ABSTRACT

The present invention discloses a fluorescent probe for detecting a sulfenated protein, which has good stability and can specifically quantitatively detect a sulfenated protein in complex biological samples, and has a good detection ability of signal-to-noise ratios, is highly sensitive, and has excellent selectivity, thereby realizing specific detection of sulfhydryl sulfenation modification of intracellular proteins.

6 Claims, 3 Drawing Sheets

(51) Int. Cl.
*C07C 303/32* (2006.01)
*C09K 11/06* (2006.01)
(52) U.S. Cl.
CPC .. *G01N 21/6486* (2013.01); *C09K 2211/1007* (2013.01); *C09K 2211/1011* (2013.01)
(58) Field of Classification Search
USPC .......................................................... 436/172
See application file for complete search history.

(56) References Cited

FOREIGN PATENT DOCUMENTS

| | | |
|---|---|---|
| CN | 105693591 A | 6/2016 |
| CN | 107235866 A | 10/2017 |
| CN | 107235866 B | 9/2019 |

OTHER PUBLICATIONS

Tan et al. "Potential Anti-AIDS Naphthalenesulfonic Acid Derivatives. Synthesis and Inhibition of HIV-1 Induced Cytopathogenesis and HIV-1 and HIV-2 Reverse Transcriptase Activities1" J. Med. Chem. 1992, 35, 4846-4863 (Year: 1992).*
Chang et al. "GMI-1070, a novel pan-selectin antagonist, reverses acute vascular occlusions in sickle cell mice" Blood. Sep. 9, 2010; 116(10): 1779-1786. (Year: 2010).*
WO, International Search Report for international patent application PCT/CN2018/085697, dated Aug. 8, 2018, 6 pages.
WO, Written Opinion of Search Report for international patent application PCT/CN2018/085697, dated Aug. 8, 2018, 4 pages.
WO, Written Opinion of Search Report for international patent application PCT/CN2018/085697, dated Aug. 8, 2018, 4 pages (English).
Huang et al., "Chemical approaches for trapping protein thiols and their oxidative modification," Acta Pharmaceutica Sinica 2012, 47 (3): 280-290.
Huang Chu-sen, "Developing Fluorescent Probes to Trap Protein Vicinal Thiols and Sulfenylation in Living Cells," (C)1994-2019 China Academic Journal Electronic Publishing House, http://www.cnki.net, PhD thesis, Jun. 11, 2012, 112 pages.
Tan GT et al., "Potential anti-AIDS naphthalenesulfonic acid derivatives. Synthesis and inhibition of HIV-1 induced cytopathogenesis and HIV-1 and HIV-2 reverse transcriptase activities," J Med Chem. Dec. 25, 1992;35(26):4846-53 DOI 10.1021/jm00104a010.
1st Office Action for Chinese patent application CN201710444443.3, dated May 4, 2018, 7 pages.
Response to 1st Office Action for Chinese patent application CN201710444443.3, dated Sep. 7, 2018, 7 pages.
2nd Office Action for Chinese patent application CN201710444443.3, dated Dec. 3, 2018, 4 pages.
Response to 2nd Office Action for Chinese patent application CN201710444443.3, dated Jan. 31, 2019, 5 pages.
3rd Office Action for Chinese patent application CN201710444443.3, dated Mar. 4, 2019, 4 pages.
Response to 3rd Office Action for Chinese patent application CN201710444443.3, dated Apr. 19, 2019, 3 pages.
International Search Report for international patent application PCT/CN2018/085697, dated Aug. 8, 2018, 4 pages with extra 3 pages of English language equivalent or summary.
Written Opinion of the International Searching Authority for international patent application PCT/CN2018/085697, dated Aug. 8, 2018, 4 pages with extra 4 pages of English language equivalent or summary.
International Preliminary Report on Patentability for international patent application PCT/CN2018/085697, dated Dec. 17, 2019, 5 pages.

* cited by examiner

FLUORESCENT PROBE FOR DETECTING SULFENYLATED PROTEIN, PREPARATION METHOD THEREOF, AND APPLICATION THEREOF

CROSS-REFERENCE TO RELATED APPLICATIONS

This application is a U.S. national phase filing of International Patent Application Serial No. PCT/CN2018/085697, entitled "FLUORESCENT PROBE FOR DETECTING SULFENATED PROTEIN, PREPARATION METHOD THEREFOR, AND APPLICATION THEREOF," which claims priority to Chinese patent application No. 201710444443.3, filed on Jun. 13, 2017, the contents of the above applications are incorporated herein by reference in their entireties for all purposes.

FIELD

The disclosure relates to the field of bio-detection, in particular, it relates to the preparation method and application of a fluorescent probe for in situ imaging the intracellular proteins, in which thiols are sulfenylated and quantitatively detecting S-sulfenylated proteins by fluorescence resonance energy transfer FRET principle.

BACKGROUND

Oxidative stress refers to under various inherent and extrinsic factors stimulate, the excessive production or metabolic block occurrence of reactive oxygen species (ROS), e.g. hydrogen peroxide, superoxide anion, alkoxy radicals, hydroxyl radicals and so on, and when the ROS cannot be eliminated effectively by the endogenous antioxidant defense system, the over accumulation of ROS participates in oxidative modification of biological macromolecules, which induces gene mutation, protein modification, lipid peroxidation, and then damaging lysosomes and mitochondria, eventually leads to cellular oxidative damage. Oxidative stress has been proven to be closely related to the occurrence of multiple systemic diseases, especially neurodegeneration such as Alzheimer's, Parkinson's, Huntington's diseases, etc. In the disease progression, oxidative stress leads to apoptosis and autophagy of brain cell which induces tissue damage and pathological changes ultimately. Thereinto, S-sulfenylated proteins are the key intermediates for protein oxidated by ROS, means that protein-thiol —SH is oxidized by ROS and transformed into sulfenic acid —SOH, which can be reduced to thiol/sulfhydryl state, or continue to be oxidized to sulfinic acid or sulfonic acid. Therefore, S-sulfenylated proteins are important transient markers of oxidative stress in organisms and cells, which are significant signals for the characterization of oxidative stress process. In recent years, sulfenylation of protein thiols becomes a new research hotspot, which attracted more and more attention of scientists. The development of methods for real-time detection of S-sulfenylated protein in organisms can greatly promote the study of biologic oxidative stress mechanism and physiopathology.

Early primary methods for detecting thiols sulfenylated modification were chromatometry and indirect approaches (Firstly, the thiols in the sample were selectively blocked, and then the sulfenic acid groups were reduced to thiols by arsenic trioxide for quantitative determination). However, the shortcomings in quantitative analysis are high detection limit or miscellaneous reaction procedures. So far, the biotin switch method is the most widely used method and most mature. Although this method is highly acceptable and accurate, there are some shortcomings, such as complicated steps, samples need to be separated and detected by mass spectrometry, difficult to use for living cell imaging and real-time monitoring and so on. It is also impossible to obtain any information such as dynamic changes after protein sulfhydryl sulfenylated modification. Nowadays, small molecule fluorescence probes imaging acts as an ideal and indispensable auxiliary tool for detecting intact biological samples, due to its high sensitivity, simple steps and can be used in vivo imaging.

However, there are some prominent problems in fluorescent small molecule probes at present: firstly, they are not stable enough for long-term storage; secondly, there is a small absorption and emission wavelength differential. And the interference from excitation spectrum could not be avoided effectively; thirdly, the sensitivity is insufficient; fourthly, the selectivity is poor, and the scope of application is not wide enough.

SUMMARY

Present disclosure provides a fluorescent probe for detecting S-sulfenylated proteins, preparation method and application thereof. Said fluorescence probe can image intracellular S-sulfenylated proteins in situ, and quantitatively detecting S-sulfenylated proteins by fluorescence resonance energy transfer FRET principle.

A fluorescent probe for detecting S-sulfenylated proteins of present disclosure having following general formula (I):

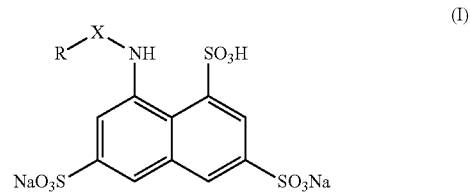

wherein X is a chemical single bond, or selected from the group consisting of

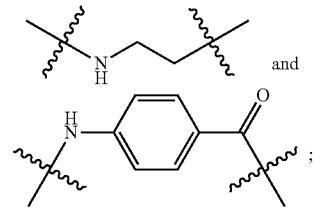

R is a group with a nucleophilic carbon atom center.

Further, in general formula I, R is selected from the group consisting of

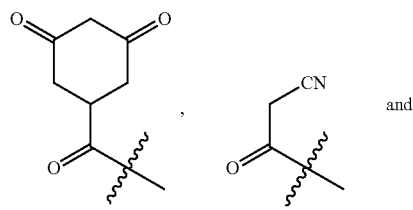

-continued

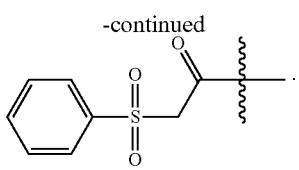

Present disclosure provides a preparation method of a fluorescent probe for detecting S-sulfenylated proteins, which is synthesized by condensation reaction of a compound capable of recognizing sulfenic acid with a fluorescent compound;

Further, the compounds capable of recognizing sulfenic acid contain a carboxylic acid with a sulfenic acid —SOH characteristic recognition group or a derivative thereof.

Further, the compounds capable of recognizing sulfenic acid contain a carboxylic acid with a sulfenic acid-SOH characteristic recognition group, which is condensed with bromoethylamine or p-aminobenzoic acid after grinding, in the presence of imidazole hydrochloride and trace water, and N,N'-carbonyldiimidazole used as the condensing agent. The chemical equation is as follows:

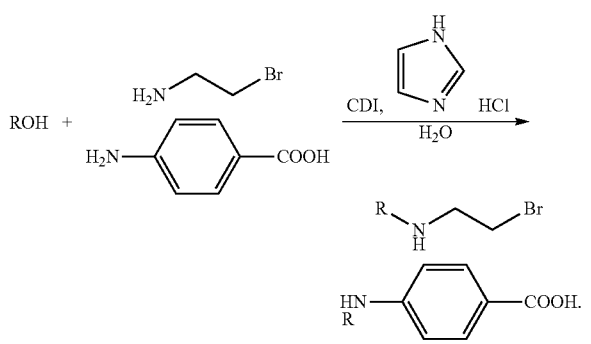

Further, the compounds capable of recognizing sulfenic acid contain a carboxylic acid with a sulfenic acid —SOH characteristic recognition group, which is condensed with 8-amino-1,3,6-naphthalenetrisulfonic acid disodium salt after grinding, in the presence of imidazole hydrochloride and trace water, and N,N'-carbonyldiimidazole used as the condensing agent. The chemical equation is as follows:

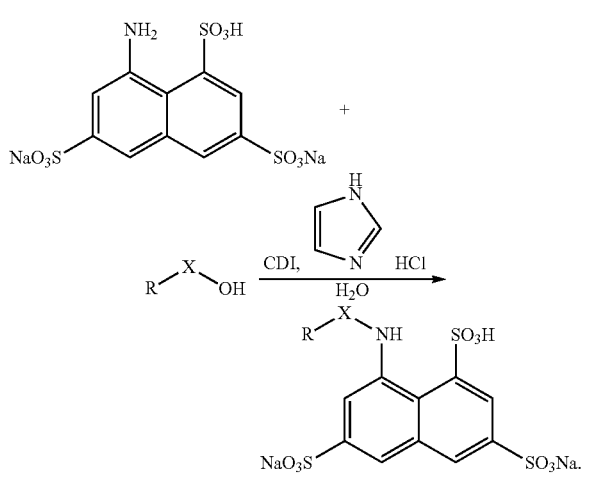

Further, the compounds capable of recognizing sulfenic acid contain a carboxylic acid derivative with a sulfenic acid-SOH characteristic recognition group, which is condensed with 8-amino-1,3,6-naphthalenetrisulfonic acid disodium salt after grinding, in the presence of imidazole hydrochloride and trace water, and triethylamine used as the condensing agent. The chemical equation is as follows:

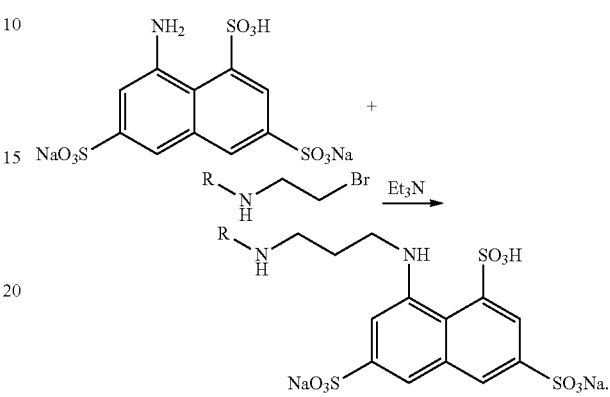

The method further comprises the steps of extraction, separation and purification after the condensation reaction.

In addition, present disclosure discloses an application of using the fluorescent probe for detecting S-sulfenylated proteins to detect the sulfenylated modification of protein sulfhydryl.

The benefits of present disclosure: The quantitative detection of S-sulfenylated proteins by small molecule fluorescence probe is based on fluorescence resonance energy transfer FRET principle. The FRET principle is: when two fluorescent chromophores are close enough, the donor molecule absorbs photons with certain frequency, and excited to a higher electronic energy state, and before which returns to the ground state, the energy is transferred to the adjacent acceptor molecule through dipole interaction. FRET occurrence conditions: a. Energy matching: The emission spectrum of the donor molecule can be absorbed by the acceptor molecule and produce a fluorescent signal. The emission spectra of donor molecule and excitation spectra of acceptor molecule must overlap significantly (>30%); B. Interaction distance: the interaction distance between donor molecule and acceptor molecule is 1-10 nm.

Present disclosure designs fluorescent probes that can react with sulfenic acid sites of proteins specifically, by using the nucleophilic substitution reaction of sulfenic acid —SOH and the compounds with nucleophilic α-carbon atoms, and these fluorescence probes emit weak fluorescence in hydrophilic environment, however, after it reacts with —SOH to form a hydrophobic adduct product with highly enhanced fluorescence, which can be used for sensitive detection of the sulfenylation of proteins. The principle of sensitive detection is that tryptophan residues in proteins act as FRET fluorescent donors, of which maximum emission wavelength is about 330 nm, meanwhile the fluorophores in small molecule fluorescence probes act as FRET fluorescent receptors, of which the excitation spectrum is about 330 nm. The FRET principle is based on the following conditions: before the reaction, the distance between the fluorophore in the small molecule fluorescent probe and the tryptophan residue in S-sulfenylated proteins can be more than 10 nm; and after the reaction, the distance between the fluorophore in the small molecule fluorescent probe and the tryptophan residue in S-sulfenylated proteins can be less than 2 nm.

The fluorescent probe of the disclosure is stable for long-term preservation and use; it is sensitive to the environment, and the fluorescence probe itself is low fluorescent in a hydrophilic environment (such as a cell cytoplasm), only after reacting with the S-sulfenylated proteins, the fluorescence group is in a hydrophobic environment within the structure of the protein to produce stronger fluorescence in order to in situ imaging the sulfhydryl sulfenylated protein in the cell. Besides, the fluorescent probe has good water solubility and large absorption emission wavelength difference, and in the extracellular buffer solution detection system, it can pair with the tryptophan residue in the protein (the emission wavelength overlaps with the excitation wavelength of the probe) to generate fluorescence resonance energy transfer FRET effect, and it can effectively avoid the interference of the exciting light and the emitted light in the protein sample, can specifically detect the S-sulfenylated proteins in a complex biological sample, and has high detection signal-to-noise ratio, good sensitivity and excellent selectivity. Thus specific identification of thiol sulfenylated modification of intracellular proteins can be achieved.

The fluorescence probe method in present disclosure is not only suitable for detecting the sulfenylated modification in cell samples, plasma and tissue homogenates, but also suitable for dynamic detection of sulfenylated modification in cells and even animal tissues.

BRIEF DESCRIPTION OF THE DRAWINGS

Present disclosure is further described below in conjunction with the drawings and embodiments.

DESCRIPTION OF THE PREFERRED EMBODIMENT

Figure 1:
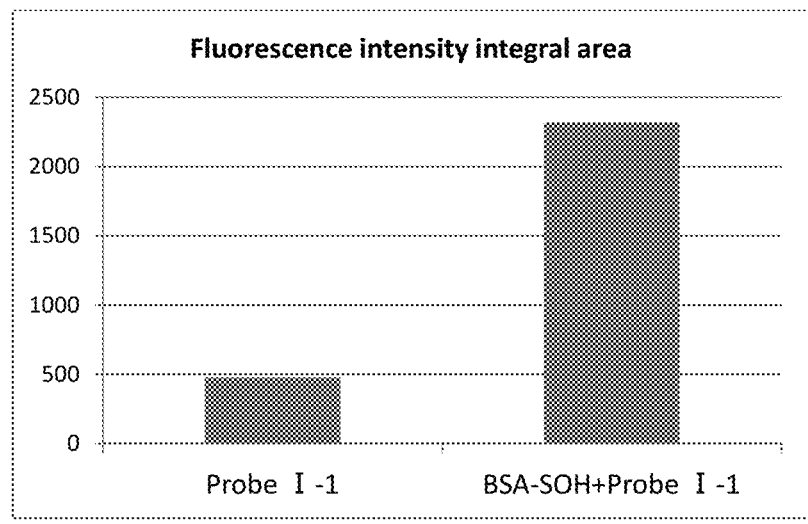
FIG. 1 shows the fluorescence change before and after reaction of the fluorescent probe molecule I-1 with bovine serum albumin S-sulfenylated proteins (BSA-SOH).

A fluorescent probe for detecting S-sulfenylated proteins of the present embodiment is represented by the following general formula (I):

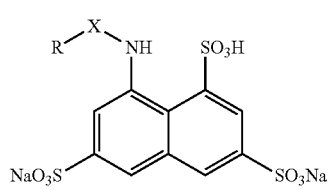

(I)

wherein X is selected from the chemical single bond,

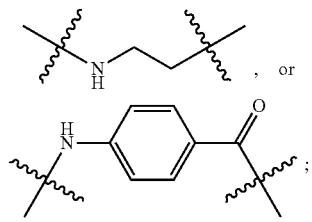

R is selected from a group having a nucleophilic carbon atom center; Said fluorescent probe for detecting S-sulfenylated proteins is stable for long-term preservation and use; and has large absorption emission wavelength difference (>170 nm); and has high detection signal-to-noise ratio, good sensitivity and excellent selectivity. "X is chemical single bond" means: R is directly linked to —NH— with a single bond.

In this embodiment, R in the structure of general formula (I) is selected from

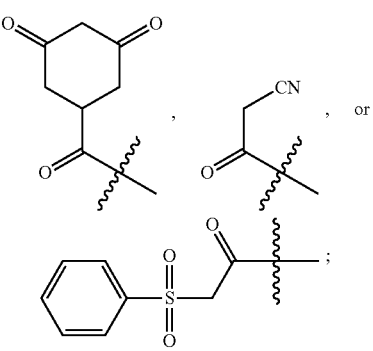

which is optimization for R. The preparation method refers to: the fluorescent probe for detecting S-sulfenylated proteins in the embodiment is synthesized by condensation reaction of a compound capable of recognizing sulfenic acid with a fluorescent compound. The standard dose of the compound capable of recognizing sulfenic acid in the reaction, such as cyanoacetic acid, is an amount just enough to complete the reaction. The method is simple and easy to operate. In this embodiment, the compounds capable of recognizing sulfenic acid is a carboxylic acid with a sulfenic acid-SOH characteristic recognition group or a derivative thereof; R can only react with sulfenic acid-SOH, and fluorescent probes that can react with sulfenic acid sites of proteins specifically is designed using the nucleophilic substitution reaction of sulfenic acid-SOH and the compounds with nucleophilic α-carbon atoms, and these fluorescence probes emit weak fluorescence in hydrophilic environment, however, after it reacts with —SOH to form a hydrophobic, highly fluorescent addition product. which can be used for sensitive detection of the sulfenylation of proteins.

In this embodiment, the compounds capable of recognizing sulfenic acid is a carboxylic acid with a sulfenic acid-SOH characteristic recognition group, which is condensed with bromoethylamine or p-aminobenzoic acid after grinding, in the presence of imidazole hydrochloride and trace water, and N,N'-carbonyldiimidazole used as the condensing agent, the chemical equation is as follows:

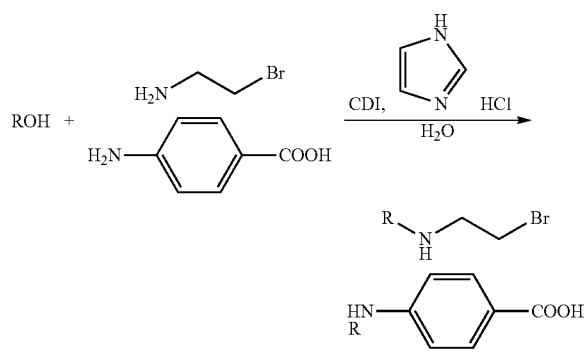

In this embodiment, the compounds capable of recognizing sulfenic acid is a carboxylic acid with a sulfenic acid-SOH characteristic recognition group, which is condensed with 8-amino-1,3,6-naphthalenetrisulfonic acid disodium salt after grinding, in the presence of imidazole hydrochloride and trace water, and N,N'-carbonyldiimidazole used as the condensing agent and the chemical equation is as follows:

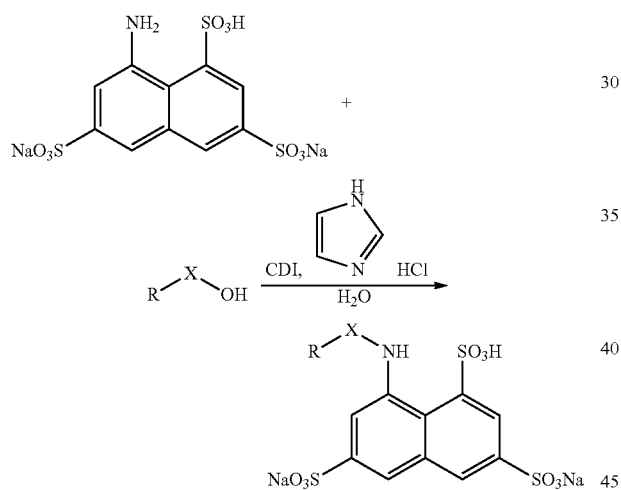

In this embodiment, the compounds capable of recognizing sulfenic acid is a carboxylic acid derivative with a sulfenic acid-SOH characteristic recognition group, which is condensed with 8-amino-1,3,6-naphthalenetrisulfonic acid disodium salt after grinding, in the presence of imidazole hydrochloride and trace water, and triethylamine used as the condensing agent, and the chemical equation is as follows:

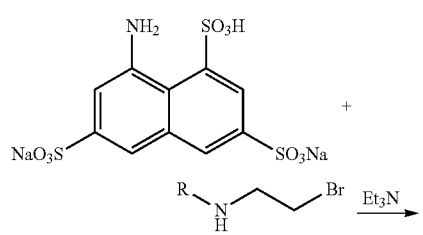

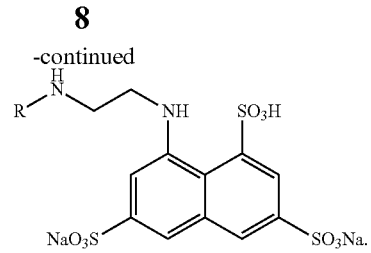

This embodiment also comprises the steps of extraction, separation and purification after the condensation reaction.

The disclosure also discloses the application of a fluorescent probe for detecting S-sulfenylated proteins in detecting the sulfenylation modification of protein thiols: Take the application of locating and visualizing intracellular S-sulfenylated proteins as an example, comprising following steps: The cells are oxidized by 100 μM hydrogen peroxide ($H_2O_2$) for 30 minutes, and the cells were fixed with 0.05% glutaraldehyde aqueous solution for 15 min, washed with PBS buffer solution for three times, and the cells were infiltrated in PBS solution, and the fluorescent probe represented by Formula I was added thereto to a final concentration of 200 μM; the cells are incubated for 4 hours at 25° C. in the dark (or shaked on the orbital incubator slowly for 30 minutes), and then the fluorescence intensity of the cells is observed and recorded. The fluorescent probe provided by present disclosure is characterized in that its fluorescent group itself has a weak fluorescence quantum yield in a hydrophilic physiological environment, and when it reacts specifically and rapidly with the —SOH group of the protein sulfonic acid in the cell, the fluorophore goes inside the hydrophobic protein structure; then the fluorescence-quantum yield of the fluorophore increases greatly, and the fluorescence enhancement is doubled to achieve specific detection and quantitative analysis of S-sulfenylated protein modification.

The following is further elaborated on the disclosure by specific embodiments.

Example 1

Preparation of Fluorescence Probe I-1 (Formula:

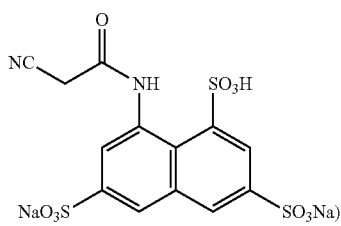

85 mg of cyanoacetic acid (85.06, 1 eq) and 178 mg of N,N'-carbonyldiimidazole CDI (162.14, 1.1 eq) were weighed and ground in a mortar at 50° C. for 5 minutes. After cyanoacetic acid reacted completely (as seen by TLC), 384 mg of 8-amino-1,3,6-trinaphthalene trisulfonate disodium hydrate (427.3, 0.9eq), 10.4 mg of imidazole hydrochloride (104, 0.1eq) and 100 μL water were added into the mortar. The mixture was ground for 10 minutes, and TLC thin layer chromatography plate was used to monitor the complete reaction of 8-Amino-1,3,6-trinaphthalene trisulfonate disodium hydrate. 10 mL of water and 3×15 mL of ethyl acetate were added, the layers were separated and the aqueous layer was lyophilized at −60° C. to give a yellow solid product I-1. HRMS (ESI-TOF) [M+Na]⁺: m/z 515.9502. ¹³C NMR (126 MHz, D$_2$O) δ 111.17, 116.77, 119.30, 119.91, 124.64, 131.52, 133.67, 135.54, 138.78, 139.57, 141.75, 144.62, 170.08.

The fluorescence change before and after reacting the fluorescent probe molecule I-1 with sulfenylated bovine serum albumin BAS-SOH A small amount of the probe was dissolved in 20 mM PBS buffer solution, and a solution of PBS buffer or sulfenylated bovine serum albumin was added respectively, so that the final concentration of the probe molecule was controlled at 10 μM, and the final concentration of the sample for testing was 10 μM. After reacting for 5 minutes, the mixture was detected by fluorospectrophotometer under the excitation of 280 nm, then the fluorescence intensity integral area of the solution was recorded and calculated at the range of emission wavelength to further determine the enhancement of the probe molecule and the fluorescence intensity after the reaction, as shown in FIG. 1.

The selectivity of the fluorescence probes I-1 for sulfenylated bovine serum albumin BSA-SOH.

Figure 2:
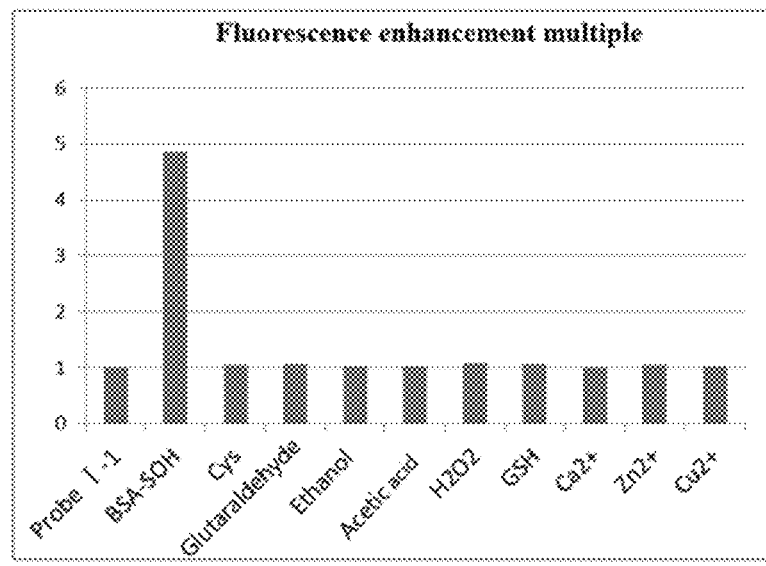
FIG. 2 shows the selectivity of the fluorescence probe I-1 for bovine serum albumin S-sulfenylated proteins (BSA-SOH).

After preparing the PBS solution-containing probe, the PBS solution containing 10 μM sample for testing was added to it to make sure the final concentration of probe is 10 μM. After reacting for 5 minutes, the mixture was detected by fluorospectrophotometer under the excitation of 280 nm, then the fluorescence intensity integral area of the solution was recorded and calculated at the range of emission wavelength for calculating the fluorescence enhancement multiple and further determine the selectivity of probe molecule to BSA-SOH, as shown in FIG. 2.

Concentration-dependent fluorescence enhancement of the fluorescence probe I-1 by bovine serum albumin S-sulfenylated proteins (BSA-SOH)

Figure 3:
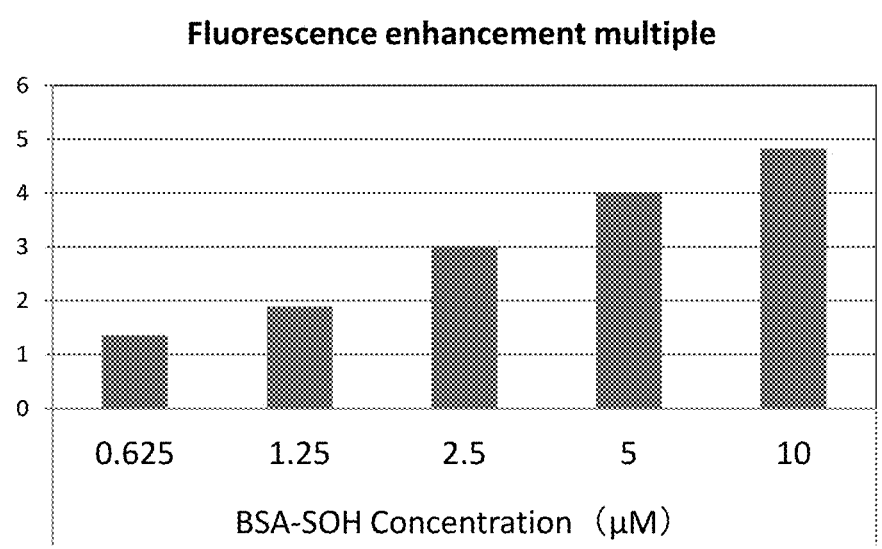
FIG. 3 shows concentration-dependent fluorescence enhancement of the fluorescence probe I-1 by bovine serum albumin S-sulfenylated proteins (BSA-SOH).

The probe was dissolved in 20 mM PBS buffer, and different concentrations of bovine serum albumin S-sulfenylated proteins solution were added respectively, and make sure the final concentration of the probe is 10 μM. After reacting for 5 minutes, the mixture was detected by fluorospectrophotometer under the excitation of 280 nm, then the fluorescence intensity integral area of the solution was recorded and calculated at the range of emission wavelength for calculating the fluorescence enhancement multiple, and further determine the fluorescence enhancement of fluorescence probe depending on the concentration of BSA-SOH, as shown in FIG. 3.

Fluorescence probes I-1 detecting the S-sulfenylated proteins in cells.

Figure 4:
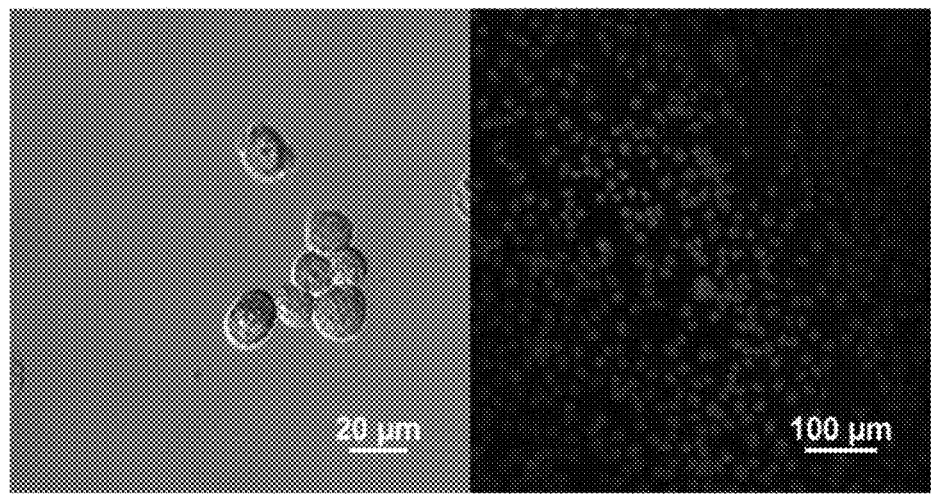
FIG. 4 shows the fluorescence probe I-1 detecting the S-sulfenylated proteins in cells.
Figure 4:
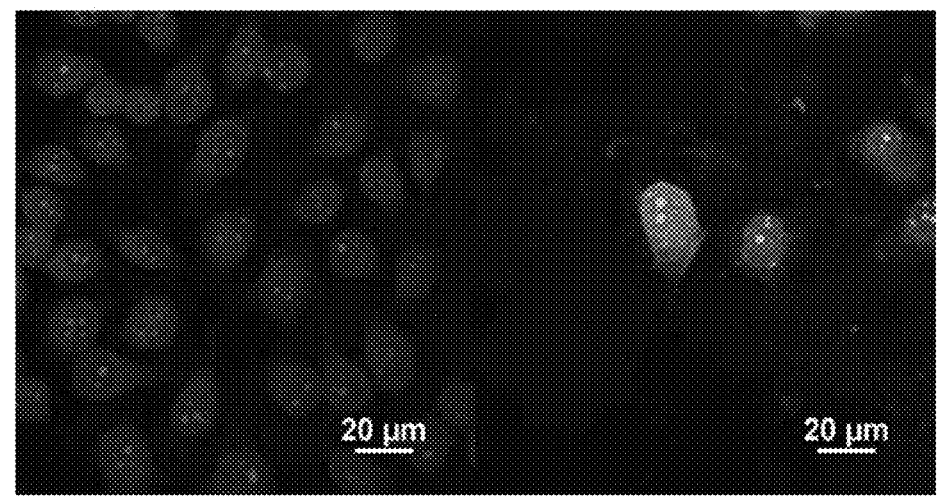

Human lung adenocarcinom cells A549 were inoculated on a medium size culture dish with 1640 medium containing 10% fetal bovine serum, and incubated in cell incubator at 37° C. for 12 hours. Then, the cells were washed with PBS buffer for three times, and hydrogen peroxide (H$_2$O$_2$) was added thereto to a final concentration of 100 μM, placed in a 37° C. cell culture incubator, and taken out after 30 minutes. Then, the cells were fixed by 200 μL of 0.05% glutaraldehyde aqueous solution, after 15 minutes, the cells were washed 1 or 2 times with PBS. The PBS solution containing fluorescent probe I-1 was added, and the final concentration was 100 μM, and then kept it for 4 hours without light. The cells were washed 2 times with 1 mL PBS solution. Laser confocal fluorescence microscopy was used to observe and take pictures. The excitation wavelength is 405 nm. The results showed that said fluorescent probe could effectively detect the sulfenic acid products of human lung adenocarcinoma cell A549, as shown in FIG. 4.

Example 2

Preparation of Fluorescence Probe I-2

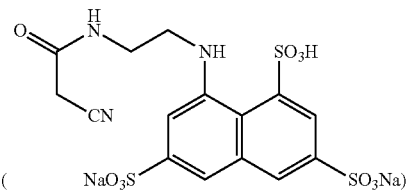

85 mg of cyanoacetic acid (85.06, 1eq) and 178 mg of N, N'-carbonyldiimidazole CDI (162.14, 1.1 eq) were weighed and ground in a mortar at 50° C. for 5 minutes. After cyanoacetic acid reacted completely (as seen by TLC), 205 mg of bromoethylamine hydrobromide (204.89, 1 eq) and 10.4 mg of imidazole hydrochloride (104, 0.1 eq) were added into the mortar, then ground for 30 minute. After that, 10 mL water and 3×15 mL dichloromethane were added, and the organic layer was collected, dried and concentrated to give an intermediate product. The intermediate product, 2 mL triethylamine and 384 mg 8-Amino-1,3,6-trinaphthalene trisulfonate disodium hydrate (427.3, 0.9eq) were added into the mortar, and the mixture was ground for 20 minutes, followed by extraction with 10 mL of water and dichlormethane (15 mL×3). After extraction, the aqueous layer was freeze-dried at −60° C. to give yellow solid I-2. HRMS (ESI-TOF) [M+Na]+: m/z 558.9416. 13C NMR (126 MHz, D2O) δ 8.34, 39.55, 46.71, 111.02, 116.42, 119.40, 124.60, 126.04, 131.36, 133.78, 135.65, 137.21, 139.97, 142.22, 169.96.

Example 3

Preparation of Fluorescence Probe I-3

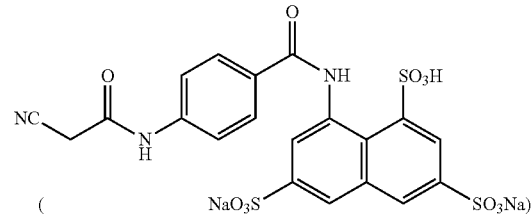

85 mg of cyanoacetic acid (85.06, 1eq) and 178 mg of N,N'-carbonyldiimidazole CDI (162.14, 1.1 eq) were weighed and ground in a mortar at 50° C. for 5 minutes. After cyanoacetic acid reacted completely (as seen by TLC), 137 mg of 4-aminobenzoic acid (137.14, 1eq) and 10.4 mg of imidazole hydrochloride (104, 0.1eq) were added into the mortar, then ground for 30 minute. After that, 10 mL water and 3×15 mL dichloromethane were added, and the aqueous layer was collected, freeze-dried at −60° C. to obtain an intermediate product. an the intermediate product and 178 mg of N,N'-carbonyldiimidazole CDI (162.14, 1.1 eq) were added into mortar, and the mixture was ground in a mortar at 50° C. for 5 minutes, and the TLC thin layer chromatography plate was used to monitor the complete reaction of cyanoacetic acid. Then, 384 mg of 8-amino-1,3,6-naphthalenesulfonic acid disodium salt hydrate (427.3, 0.9 eq), 10.4 mg of imidazolium hydrochloride (104, 0.1 eq) and 100 μL of water were added into the mortar, and ground for 10 minutes, and the TLC thin layer chromatography plate was used to monitor the complete reaction of 8-amino-1,3,6-naphthalenesulfonic acid disodium salt. 10 mL of water and dicholormethane (15 mL×3) were added for extraction, and the aqueous layer was freeze-dried at −60° C. to give yellow solid I-3. HRMS (ESI-TOF) [M+Na]+: m/z 634.9333°, 13C NMR (126 MHz, D2O) δ 8.04, 46.36, 110.91, 114.79, 116.39, 118.76, 120.41, 124.45, 127.77, 129.95, 130.68, 131.17, 134.64, 135.37, 137.25, 138.91, 139.74, 140.69, 141.90, 144.65, 154.10, 164.84, 169.79, 174.72.

Example 4

Preparation of Fluorescence Probe I-4

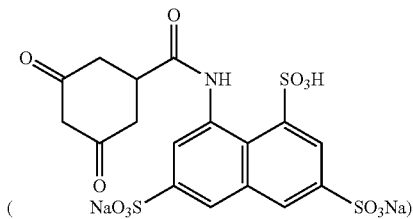

156 mg of 3,5-dicarbonylcyclohexanoic acid (156.14, 1eq) and 178 mg of N,N'-carbonyldiimidazole CDI (162.14, 1.1 eq) were weighed and ground in a mortar at 50° C. for 5 minutes. After the 3,5-dicarbonylcyclohexanoic acid reacted completely (as seen by TLC), 384 mg of 8-amino-1,3,6-naphthalenesulfonic acid disodium salt hydrate (427.3, 0.9eq), 10.4 mg of imidazole hydrochloride (104, 0.1eq) and 100 μL of water were added into the mortar, then ground for 10 minute, and the TLC thin layer chromatography plate was used to monitor the complete reaction of 8-amino-1,3,6-naphthalenesulfonic acid disodium salt. After that, 10 mL water and 3×15 mL ethyl acetate were added, the layers were separated and the aqueous layer was collected, freeze-dried at −60° C. to obtain the yellow solid I-4. HRMS (ESI-TOF) [M+Na]+: m/z 586.9218. 13C NMR (126 MHz, D2O) δ37.56, 42.54, 99.99, 111.26, 116.93, 118.98, 120.05, 124.71, 131.66, 133.35, 135.63, 138.77, 139.54, 141.73, 144.62, 182.66, 197.71.

Example 5

Preparation of Fluorescence Probe I-5

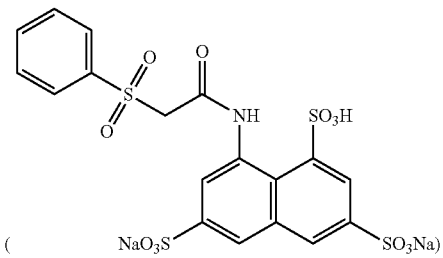

200 mg of benzenesulfonylacetic acid (200.22, 1 eq) and 178 mg of N,N'-carbonyldiimidazole CDI (162.14, 1.1 eq) were weighed and ground in a mortar at 50° C. for 5 minutes. After the benzenesulfonylacetic acid reacted completely (as seen by TLC), 384 mg of 8-amino-1,3,6-naphthalenesulfonic acid disodium salt hydrate (427.3, 0.9 eq), 10.4 mg of imidazole hydrochloride (104, 0.1 eq) and 100 μL of water were added into the mortar, then ground for 10 minute, and the TLC thin layer chromatography plate was used to monitor the complete reaction of 8-amino-1,3,6-naphthalenesulfonic acid disodium salt. After that, 10 mL water and 3×15 mL ethyl acetate were added, the layers were separated and the aqueous layer was freeze-dried at −60° C. to obtain the yellow solid I-5. HRMS (ESI-TOF) [M+Na]+: m/z 630.8895.

Finally, it is stated that the embodiments above are only used to illustrate the technical scheme in present disclosure, not to limit it. Although present disclosure is described in detail referring to optimal embodiments, it should be understood by general technicians in the field that the technical scheme in present disclosure could be modified or replaced equally without departing from the purpose and scope of present disclosure technical scheme. The technical scheme that is modified or replaced equally should be covered in the scope of claims of this disclosure.

The invention claimed is:

1. A fluorescent probe for detecting S-sulfenylated proteins, having following formula (I):

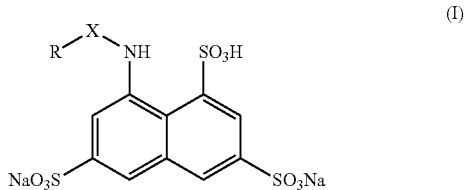

(I)

wherein X is a chemical single bond,

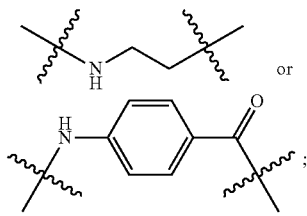

or ;

wherein the R is a group selected from the set consisting of

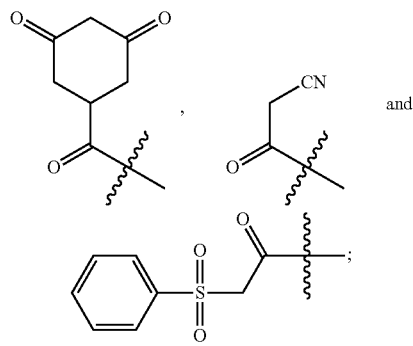

, and ;

and R is connected to the NH of X when X is

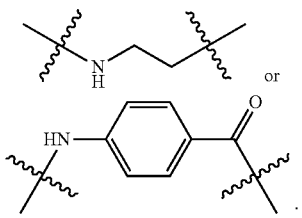

2. A method of preparing the fluorescent probe for detecting S-sulfenylated proteins of claim 1, wherein the fluorescent probe for detecting S-sulfenylated proteins is synthesized by a condensation reaction of a compound capable of recognizing sulfenic acid with a fluorescent compound.

3. The method according to claim 2, wherein the compound capable of recognizing sulfenic acid is carboxylic acid with a sulfenic acid-SOH characteristic recognition group or a derivative thereof.

4. The method according to claim 3, wherein the compound capable of recognizing sulfenic acid is a carboxylic acid with a sulfenic acid-SOH characteristic recognition group, which is condensed with bromoethylamine or p-aminobenzoic acid after grinding, in the presence of imidazole hydrochloride and trace water, and N, N'-carbonyldiimidazole used as the condensing agent; the chemical reaction equation is as follows:

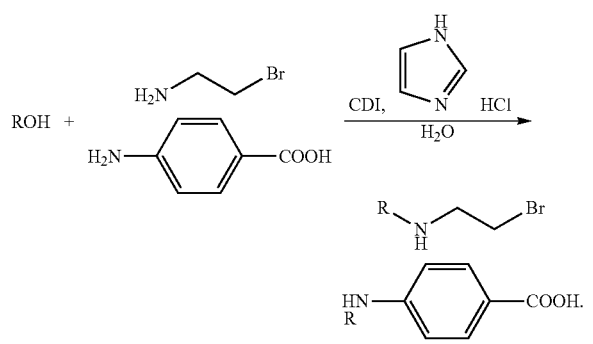

5. The method according to claim 3, wherein the compound capable of recognizing sulfenic acid is a carboxylic acid with a sulfenic acid-SOH characteristic recognition group, which is condensed with
8-amino-1,3,6-naphthalenetrisulfonic acid disodium salt after grinding, in the presence of imidazole hydrochloride and trace water, and N, N'-carbonyldiimidazole used as the condensing agent; the chemical reaction equation is as follows:

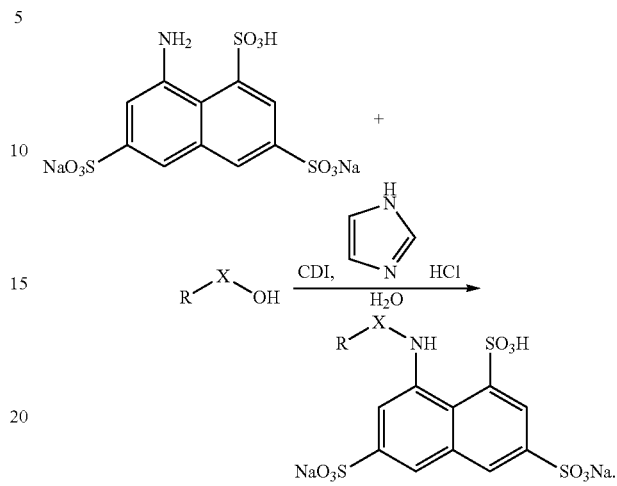

6. The method according to claim 3, wherein the compound capable of recognizing sulfenic acid is a carboxylic acid derivative with a sulfenic acid-SOH characteristic recognition group, which is condensed with 8-amino-1,3,6-naphthalenetrisulfonic acid disodium salt after grinding, in the presence of imidazole hydrochloride and trace water, and triethylamine used as the condensing agent;

the chemical equation is as follows:

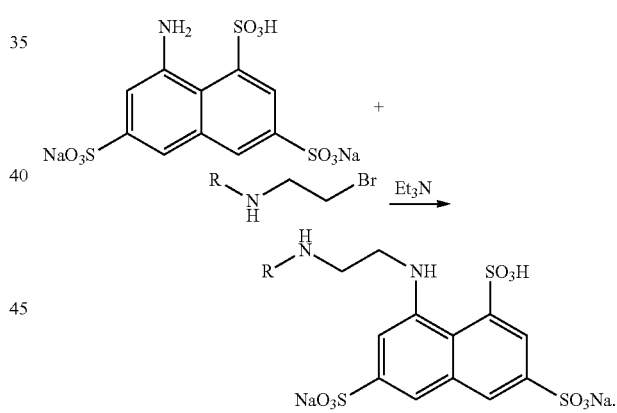

* * * * *